(12) United States Patent
Ray et al.

(10) Patent No.: US 8,435,969 B2
(45) Date of Patent: May 7, 2013

(54) METHOD AND COMPOSITIONS FOR TREATING HEMATOLOGICAL MALIGNANCIES

(75) Inventors: Adrian S. Ray, Redwood City, CA (US); Daniel B. Tumas, San Carlos, CA (US); Hans Reiser, San Francisco, CA (US); William J. Watkins, Saratoga, CA (US); William A. Lee, Los Altos, CA (US); Lee S. Chong, Newark, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 13/070,179

(22) Filed: Mar. 23, 2011

(65) Prior Publication Data

US 2011/0172192 A1     Jul. 14, 2011

Related U.S. Application Data

(62) Division of application No. 11/803,822, filed on May 16, 2007, now abandoned.

(60) Provisional application No. 60/800,983, filed on May 16, 2006, provisional application No. 60/831,805, filed on Jul. 18, 2006.

(51) Int. Cl.
*A61K 31/675* (2006.01)
*C07F 9/6561* (2006.01)

(52) U.S. Cl.
USPC ............................................. 514/81; 544/244

(58) Field of Classification Search .................. None
See application file for complete search history.

(56) References Cited

U.S. PATENT DOCUMENTS

| | | | | |
|---|---|---|---|---|
| 5,795,909 | A * | 8/1998 | Shashoua et al. | 514/449 |
| 6,844,349 | B2 * | 1/2005 | Kath et al. | 514/266.21 |
| 2003/0045583 | A1 * | 3/2003 | Hadfield et al. | 514/649 |
| 2003/0149044 | A1 * | 8/2003 | Quallich et al. | 514/249 |
| 2003/0229225 | A1 | 12/2003 | Reddy et al. | |
| 2005/0222090 | A1 * | 10/2005 | Cheng et al. | 514/81 |
| 2006/0281759 | A1 * | 12/2006 | de Diego et al. | 514/255.03 |
| 2007/0149479 | A1 * | 6/2007 | Fischer et al. | 514/58 |
| 2007/0149552 | A1 * | 6/2007 | Ku et al. | 514/259.31 |
| 2009/0258840 | A1 * | 10/2009 | Chong et al. | 514/81 |

FOREIGN PATENT DOCUMENTS

| | | |
|---|---|---|
| WO | WO-02/08241 | 1/2002 |
| WO | WO-2005/066189 | 7/2005 |
| WO | WO-2005/072748 | 8/2005 |

OTHER PUBLICATIONS

Keith et al., Antimicrobial Agents and Chemotherapy (2003), 47(7), 2193-2198.*
NZ Office Action for Patent Application No. 572368, dated Jun. 11, 2010.
CN Office Action for Patent Application No. 200780017637.X, dated Jul. 8, 2010.
CN Office Action for Application No. 200780017637.X, dated Dec. 21, 2010.
Andrei, G. et al. (1998) "Antiproliferative Effects of Acyclic Nucleoside Phosphonates on Human Papillomavirus (HPV)-Harboring Cell Lines Compared with HPV-Negative Cell Lines" Oncology Res. 10:523-531.
Kast, R. (2003) "Tenofovir, COX Inhibitors and Zileuton During Cancer Immunotherapies: Up-Regulated TNF-alpha Increases Antigen Driven Lymphocyte Proliferation" Mole Immuno. 40:297-303.
O'Neil, M. et al. (2001) "The Merck Index Thirteenth Edition" Merck & Co. Inc. Whitehouse Station, N.J. p. 29.
O'Neil, M. et al. (2001) "The Merck Index Thirteenth Edition" Merck & Co. Inc. Whitehouse Station, N.J. p. 1362, col. 1 & 1631, col. 2.
Hatse, et al. (1999) "N6-Cyclopropyl-PMEDAP: A Novel Derivative of 9-(2- Phosphonylmethoxyethyl)-2,6-diaminopurine (PMEDAP) with Distinct Metabolic, Ntiproliferative, and Differentiation-Inducing Properties" Biochm. Pharma 58:311-323.
Valerianova, M. et al. (2001) "Antitumour Activity of N6-Substituted PMEDAP Derivatives Against T-Cell Lymphoma" Anticancer Res. 21:2047-2064.
Erasian Office Action for Application No. 200802333/28, mailed Jun. 29, 2011.
MX Office Action for Application No. MX/a/2008/014665, dated Jun. 16, 2011.
CN Office Action for Application No. 200780017637.X dated Oct. 26, 2011.
Amended Claims as Filed for Eurasian Application No. 200802333 dated Mar. 15, 2012.

* cited by examiner

*Primary Examiner* — Mark Berch
(74) *Attorney, Agent, or Firm* — J. Elin Hartrum; Francis O. Ginah

(57) ABSTRACT

A compound of formula 1

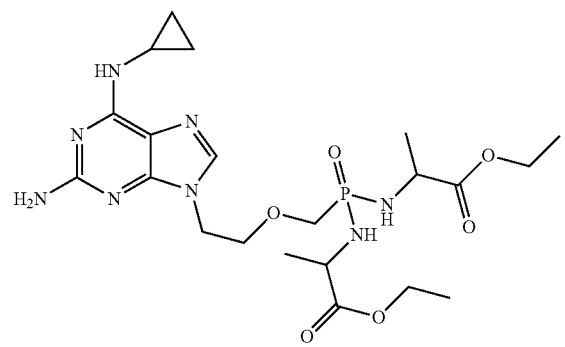

and/or its salts, tautomers or solvates is used to treat hematological malignancies. In an embodiment, an organic acid salt of compound 1 is provided for general use in treatment of neoplasms, and in a further embodiment the salt is stabilized with carbohydrate.

1 Claim, No Drawings

METHOD AND COMPOSITIONS FOR TREATING HEMATOLOGICAL MALIGNANCIES

CROSS-REFERENCE TO RELATED APPLICATIONS

The present application is a divisional application of U.S. application Ser. No. 11/803,822, filed May 16, 2007, which claims priority to U.S. Provisional Application No. 60/800,983, filed May 16, 2006, and also claims priority to U.S. Provisional Application No. 60/831,805, filed Jul. 18, 2006, the contents of which are incorporated herein by reference in their entirety.

BACKGROUND OF THE INVENTION

N-6 cyclopropylPMEDAP ("cpr-PMEDAP") has been shown to be effective producing an antiproliferative and differentiation-inducing effect in in vitro cell culture against a variety of tumor cell lines (Naessens et al., "Biochem. Pharmacol. 1999 Jul. 15; 58(2):311-23). However, when cpr-PMEDAP and other N6-substituted. PMEDAP compounds were employed in an in vivo model of haematological malignancy of inbred Sprague-Dawley rats (Valerianova et al. "Anticancer Res. 2001 May-June; 21(3B):2057-64), the authors concluded that the "acyclic nucleoside phosphonates substituted at the 6-position of 2,6-diaminepurine ring do not seem to be promising drugs for the treatment of haematological malignancies" due to "high toxicity".

Various bis- and mono-amino acid amidate esters of cpr-PMEDAP (and their use as antiproliferative agents) have been disclosed. See WO 05/066189. WO 02/08241 discloses a method for screening methoxyphosphonate nucleotide analogue prodrugs that are useful for treating hematological malignancies with reduced toxicity.

Hematological malignancies are broadly defined as proliferative disorders of blood cells and/or their progenitors, in which these cells proliferate in an uncontrolled manner. Anatomically, the hematologic malignancies are divided into two primary groups: lymphomas—malignant masses of lymphoid cells, primarily but not exclusively in lymph nodes, and leukemias—neoplasm derived typically from lymphoid or myeloid cells and primarily affecting the bone marrow and peripheral blood. The lymphomas can be sub-divided into Hodgkin's Disease and Non-Hodgkin's lymphoma (NHL). The later group comprises several distinct entities, which can be distinguished clinically (e.g. aggressive lymphoma, indolent lymphoma), histologically (e.g. follicular lymphoma, mantle cell lymphoma) or based on the origin of the malignant cell (e.g. B lymphocyte, T lymphocyte). Leukemias and related malignancies include acute myelogenous leukemia (AML), chronic myelogenous leukemia (CML), acute lymphoblastic leukemia (ALL) and chronic lymphocytic leukemia (CLL). Other hematological malignancies include the plasma cell dyscrasias including multiple myeloma, and the myelodysplastic syndromes.

While the introduction of novel agents such as imatinib (Gleevec®), bortezomib (Velcade®) and rituximab (Rituxin®) has improved the outcome of several hematological malignancies, there remains an unmet medical need for novel, efficacious therapeutics. For example, there is an unmet medical need for patients suffering from treatment-refractory/relapsed NHL, as the incidence of NHL has risen substantially in the United States over the past five decades.

Leukemias have lower patient numbers. However, there remains substantial unmet medical need, for example for the treatment of acute myelogenous leukemia (AML) and chronic lymphocytic leukemia (CLL), as illustrated by poor 5-year survival rates.

There is a need for multi-specific or broadly active antimetabolic agents with an improved therapeutic window over existing treatment modalities, which can be used either as stand-alone monotherapy or in combination with other therapeutics. Most antimetabolites either interfere with enzymes involved in DNA synthesis, such as the enzymes concerned with thymidine or purine biosynthesis, and/or are incorporated into newly synthesized DNA. Nucleobase, nucleoside, and nucleotide analogs are an important class of effective cytotoxic drugs, and are widely used for the treatment of leukemias and lymphomas. Some of these agents, 5-fluorouracil, capecitabine, and especially gemcitabine, are also being used for the treatment of solid tumors. Three adenosine analogs, fludarabine, cladribine, and clofarabine, are indicated for CLL, hairy-cell leukemia, and pediatric ALL, respectively. The purine analog, pentostatin (2'-deoxycoformycin), an inhibitor of adenosine deaminase, has clinical activity against lymphoid malignancies. Nelarabine is a prodrug of the deoxyguanosine analogue ara-G, which is resistant to catabolism by purine nucleoside phosphorylase and has demonstrated activity against T-cell malignancies. Amongst the pyrimidine analogs, cytarabine (ara-C) has been evaluated; it is active in a number of hematologic malignancies and is one of the agents used in the treatment of acute myelogenous leukemia.

However, existing therapies have limitations with regard to, for example, safety, efficacy and ease of use. It is not uncommon for treatments to be successful initially, then have the hematological malignancies frequently relapse over time.

Therefore, there remains a need for novel nucleosides/nucleotides with an improved therapeutic window and/or complimentary utility over existing compounds in this class.

Applicants sought a compound suitable for the treatment of hematological malignancies with improved PK and loading, improved therapeutic window and/or lower drug resistance. In particular it was desired to identify a compound that would concentrate in blood cells, in particular PBMCs. Concentrating the compound in these target cells would be expected to widen the therapeutic window by reducing the exposure of the patient's other tissues to the compound.

WO 05/066189 discloses a compound having structure 1:

(1)

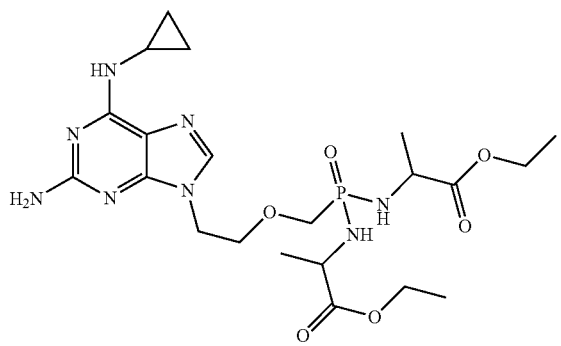 [SMILES: CCOC(=O)C(C)NP(=O)(COCCn1cnc2c(NC3CC3)nc(N)nc21)NC(C)C(=O)OCC]

This invention relates to compound 1. It also relates to the diastereomer thereof in which the bis amino acid substituted on the phosphorus atom is an L amino acid, as well as such diasteromer substantially free of D amino acid.

Heretofore compounds of formula I have been employed as the free base. However, applicants determined that the free base is not commercially optimal for formulation into a dosage form because the free base is hygroscopic. Accordingly applicants sought a form of compound 1 which could facilitate manufacturing processes for therapeutic dosage forms.

SUMMARY OF THE INVENTION

Applicants have found that the nature of the alkyl ester on the carboxyl group of the amino acid ester of the cpr-PMEDAP bisamidate class of compounds is instrumental in preferentially distributing the compound into PBMCs. Unexpectedly, it was found that administering the bis(ethyl) ester (i.e., compound 1) resulted in a highly preferential distribution of cpr-PMEDAP into the PBMCs over plasma. The distribution was far superior to that obtained with the otherwise closely related bis(isopropyl) ester. In addition, it was determined that the organic acid salts of compound 1 were less hygroscopic than the free base, thereby facilitating the manufacture of products containing compound 1. Finally, it was determined that the stability of these salts (particularly in parenteral formulations) was enhanced by including a carbohydrate in the formulations.

Accordingly, one embodiment of the invention is an organic acid salt of compound 1 and/or its tautomers and solvates.

Another embodiment of the invention is a composition comprising (a) an organic acid salt of compound 1 and/or its tautomers and solvates and (b) a carbohydrate, whereby storage stability of the salt is enhanced.

Another embodiment of the invention is a method for the treatment of a patient having a hematological malignancy comprising administering to the patient a therapeutically effective amount of the compound

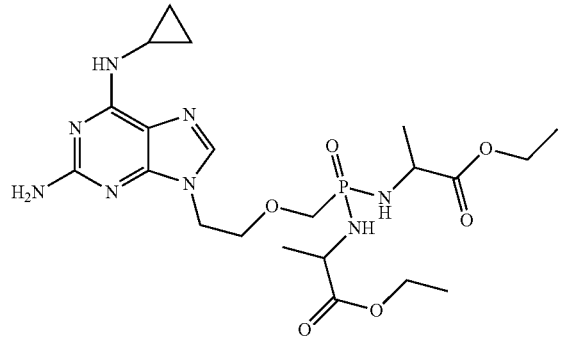 [SMILES: CCOC(=O)C(C)NP(=O)(COCCn1cnc2c(NC3CC3)nc(N)nc21)NC(C)C(=O)OCC]

and/or its salts, tautomers and solvates.

A further embodiment of the invention is a combination comprising the compound

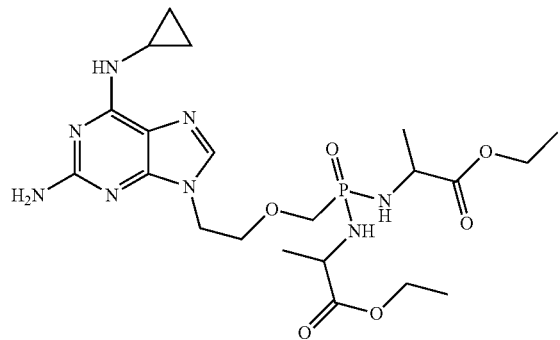

and/or its salts, tautomers and solvates in a container suitable for use in parenteral administration of the compound.

A further embodiment of the invention is a method comprising preparing an organic acid salt of the compound

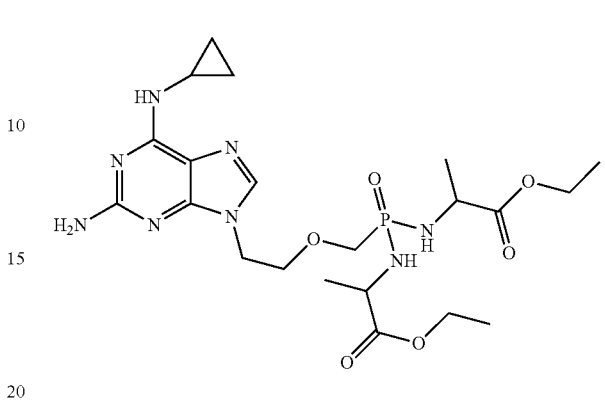

and a carbohydrate in a sterile aqueous solution, and storing said solution for a period exceeding about 1 hour.

A further embodiment of the invention is a packaged composition comprising a sterile aqueous solution of a carbohydrate and an organic acid salt of the compound

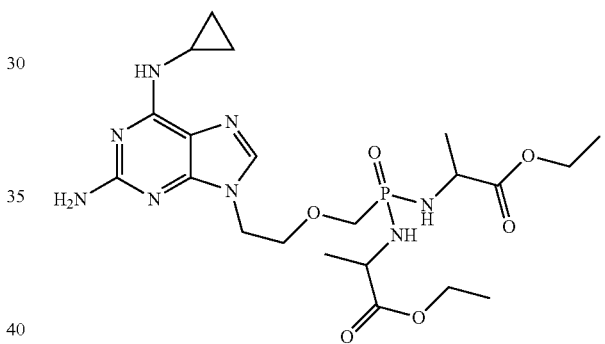

together with a disclosure (e.g. a patient insert) that the solution optionally is stored for a period of greater than about 1 hour.

Suitable organic acids for preparing the salts of this invention typically are compounds containing at least one carboxyl group, including amino acids (naturally occurring or synthetic) such as glutamic acid and aspartic acid, and $C_{1-16}$ alkyl and $C_{6-16}$ aryl and $C_{4-16}$ heteroaryl carboxylic acids such as acetic, glycolic, lactic, pyruvic, malonic, glutaric, tartaric, citric, fumaric, succinic, malic, maleic, hydroxymaleic, benzoic, hydroxybenzoic, phenylacetic, cinnamic, salicylic and 2-phenoxybenzoic acids, together with any derivative (excluding esters where no carboxyl remains free) thereof having the same root (e.g., "acetoacetic acid") which is disclosed in the table "Physical Constants of Organic Compounds" pp 3-12 to 3-523 Merck Index $74^{th\ Ed.}$ 1993. Dicarboxylic organic acids are of particular interest. It is within the scope of this invention to employ more than one organic acid in combination. The salts are prepared in analogy to the procedure shown in example 1 below.

Typically, the molar ratio of organic acid to compound 1 is about 1:1. However, the ratio may be as great as 1 mole of compound 1 to the number of acid groups in the case of polyorganic acids, e.g., a 2:1 ratio of compound 1 to salt for a dicarboxylic acid salt. However, the proportion is variable, ranging down to 1:1 or less, depending upon the enrichment of the acid functionality and its degree of substitution with acidic functionalities.

Suitable formulations of compound 1, whether for veterinary and for human use, optionally comprise one or more acceptable carriers. The carrier(s) must be "acceptable" in the sense of being compatible with the other ingredients of the formulation and physiologically innocuous to the patient.

Formulations optionally will contain excipients such as those set forth in the "Handbook of Pharmaceutical Excipients" (1986). Excipients optionally include ascorbic acid and other antioxidants, chelating agents such as EDTA, carbohydrates such as dextrin, mannitol or dextrose, buffers (e.g., citrate), alkali metal salts, glidants, bulking agents and other substances conventionally found in tablets, capsules, solutions or other compositions suited or intended for therapeutic use. Typically the formulations will not contain conventional tabletting excipients since they usually are formulated for parenteral use. The formulations ideally will be sterile. In addition, parenteral preparations will be substantially isotonic. The pH of the formulations optionally ranges from about 5-10, ordinarily about 6-9, typically about 5-6.

Parenteral (sterile aqueous) solutions of the organic acid salts of compound 1 optionally comprise a stabilizing amount of carbohydrate, typically a saccharide (mono, di or polysaccharides), glycoside or sugar alcohol (alditols). Polysaccharides should be biodegradable upon parenteral injection or infusion and include dextrins and starches, typically 3-10 units. Representative carbohydrates include hexoses, aldoses, aldohexoses, aldotrioses (e.g. glyceraldehyde), aldotetroses (e.g. erythrose), aldopentoses (e.g. arabinose), ketoses, ketohexose (e.g. fructose), ketopentoses (e.g. ribulose), maltose, sucrose, lactose, ribose, xylose, lyxose, allose, altrose, glucose, mannose, gulose, idose, galactose and talose. Of particular interest are carbohydrates conventionally used in parenteral formulations, e.g., mannitol or dextrose. The optical character of the carbohydrate is not critical, but it is desirable for the configuration to be such that the carbohydrate is biodegradable upon parenteral administration. For example, 5% dextrose (by weight of solution; pH about 4.2, unbuffered) permits storage of compound 1 succinate at 40° C. for 60 hours without significant degradation. On the other hand, storage in buffered solutions at pH 2, 7 and 9 under the same conditions lead to substantial degradation of compound 1: About 100%, 18% and 76% by weight, respectively.

The stabilizing amount of carbohydrate is variable and will depend upon the expected storage conditions and desired shelf life, buffer choice, pH, amount of compound 1, and other factors that will be appreciated by the artisan. Usually, about from 0.5% to 5% by weight of solution will be used. Typically the optimal amount of carbohydrate will be determined by routine experimentation, but the amount generally will not exceed (along with buffers, sodium chloride and the like) an amount that provides isotonicity to the solution. Hyperisotonic concentrates are acceptable, however, if it is expected to dilute the parenteral composition prior to or during infusion. The parenteral solution optionally is buffered (typically with citrate buffer) at about pH 4 to 6.

The presence of carbohydrate stabilizes the salts of compound 1 in aqueous solution for storage (including administration time) of at least about 60 hours, up to 1 week, 1 month or 1 year, or any intermediate period, depending upon the factors noted above for the concentration of carbohydrate, e.g., the storage temperature and the like.

The therapeutic compositions optionally are administered by parenteral routes (including subcutaneous, intramuscular, intravenous, intradermal, intrathecal and epidural) since these are the most convenient for treatment of malignancies. Intravenous infusions are generally the administration method of choice.

The formulations are presented in unit-dose or multi-dose containers, for example sealed ampoules, vials or flexible infusion bags. The containers optionally will be glass or rigid plastic, but typically will be semirigid or flexible containers fabricated from polyolefins (polyethylene) or plasticized polyvinylchloride. The container is typically single chambered. These containers have at least one integral sterile port to facilitate the sterile entry into the container of a device for accessing the contents (usually syringes or an intravenous set spike). The port provides sterile access for solubilizing solution (if required) and egress of parenteral solutions. An overpouch (usually polyolefin) is optionally provided for the container.

The formulation is present in the container as a solution or in dry form. If stored in a substantially anhydrous form, e.g., lyophilized, the formulation will require only the addition of the sterile liquid carrier, for example water for injection, immediately prior to use. Solutions include tonicity establishing agents such as sodium chloride or a sugar such as mannitol or dextrose. An unexpected advantage of carbohydrate or sugar is an increase in stability of compound 1 salt in stored aqueous solutions. The containers are filled with sterile solution or are filled and then sterilized, e.g., by heat or chemical agents, in accord with known processes. In general, a sterile solution of the formulation is sterile-filled into a flexible container and thereafter optionally lyophilized. Suitable technology for producing the container products of this invention is found in Avis et al., *Pharmaceutical. Dosage Forms: Parenteral Medications vols.* 1 and 3 (1984).

The parenteral containers will contain a daily dose or unit daily sub-dose of compound 1 as described below, or an appropriate fraction thereof.

Compound 1, the organic acid salts of Compound 1, or aqueous solutions thereof stabilized by carbohydrate, optionally are employed to treat any neoplasm, including not only hematologic malignancies but also solid tumors of all kinds, e.g., head and neck, lung, kidney, liver, bone, brain and the like, particularly uterine and cervical cancer and dysplasia, melanoma, and cancers of the breast, colon, prostate, lung (small cell and non-small cell) and pancreas.

The formulations of this invention are administered either as monotherapy or in combination with other agents for the treatment of hematological malignancies. The formulation of this invention optionally is administered to the patient at substantially the same time as other antineoplastic agent(s), or the agent(s) is combined with the formulation of this invention and then administered simultaneously to the patient. Typical antineoplastic agents useful with compound 1 (either combined therewith in therapeutically effective amounts or administered concurrently) include any of the therapeutics currently employed in the treatment of malignancies, including those used for hematologic malignancies that are mentioned in the background above. These companion agents are administered (a) at substantially the same time but by different administration routes, (b) are combined with the formulation of this invention and administered concurrently, or (c) are administered during alternative periods (for instance during a resting period from treatment with compound 1). In general, if used in combination, the formulation of this invention is therapeutically combined with another antineoplastic agent selected from a distinct class, e.g., a monoclonal antibody.

Treatment of NHL typically includes cyclophosphamide, doxorubicin, vincristine, prednisone and rituximab. If used in combination, Compound 1 is administered in a course of therapy together with, or as a replacement of, one or more of the foregoing agents. Compound 1 may also be administered in combination with rituximab. For the therapy of CLL, administer Compound 1 either as monotherapy or in combination with other agents, such as cyclophosphamide and/or rituximab. Other therapeutic agents suitable for use with compound 1 include etoposide, melphalan, nitrosurea, busulfan, platinum complexes, nonclassic alkylators such as procarbazine, antimetabolites such as folate, purines, adenosine analogues, pyrimidine analogues, vinca alkyloides, and the like.

Based on single dose toxicology observations in dogs, it is reasonable to assume that a dose of compound 1 of between 1 mg/kg/day and 3 mg/kg or greater up to approximately 10 mg/kg day would be efficacious in dogs (when using an organic acid salt of compound 1, the dose would be adjusted to take account of the additional weight of the salt). Assuming that the PK profile of the compound in humans is similar to that observed in dogs, the findings to date suggest a human efficacious dose for compound 1 (corrected for surface area by the factor of 0.54) of between 0.54 mg/kg IV and 1.62 mg/kg IV or greater, administered as a single dose with repeat dosing at interims of approximately 1 to 14 days, generally weekly or every 2 weeks, typically weekly for 2 doses, depending upon the condition of the patient and tolerance to the infusion, among other factors. Since considerable variation should be expected in suitable doses because of the unique nature of individual cancers, the condition of the patient, patient tolerance and other matters known to the ordinary oncologist, the range of effective doses will be larger than the core experimental model. Thus, a dosage range of about from 0.5 to 5.4 mg/kg/day is expected to be suitable. A single dose is suitable, but multiple cycles of dosing are anticipated to be typical, with a resting period of about 10-30, usually 23, days between cycles, again depending upon the condition of the patient and tolerance to the therapeutic as will be apparent to the ordinary artisan.

All literature and patent citations above are hereby expressly incorporated by reference. The invention has been described in detail sufficient to allow one of ordinary skill in the art to make and use the subject matter of the following claims. The following examples exemplify the present invention, and are not to be construed to limit the present invention.

EXAMPLE 1

A mixture of cPrPMEDAP (1.64 g, 5 mmol), Ala-ethyl ester. HCl (4.62 g 30 mmol) and TEA (8.36 mL, 60 mmol) was treated with 10 mL of anhydrous pyridine and heated to 60° C. to reach a homogenous solution. A solution of Aldrithiol-2 (7.78 g, 35 mmol) and triphenylphosphine (9.18 g, 35 mmol) in 10 mL of anhydrous pyridine was added. The resulting mixture was heated at 60° C. overnight. After cooling, the bright yellow solution was poured into saturated aqueous sodium bicarbonate and extracted with ethyl acetate. The organic layer was washed with brine, then dried over sodium sulfate. After removal of solvent, the crude residue was purified by flash chromatography using 100% ethyl acetate then switched to 10-15% MeOH/DCM to elute the desired product (1.12 g, 43% yield).

Succinate Salt Formation:

The neutral prodrug (2.60 g) was dissolved in a solution of succinic acid (583 mg) in ethanol (15 mL). Following the addition of 50% v/v n-heptane/ethanol (20 mL), the desired salt was isolated by filtration (2.26 g; M.P. 130° C.).

Chemical Structure

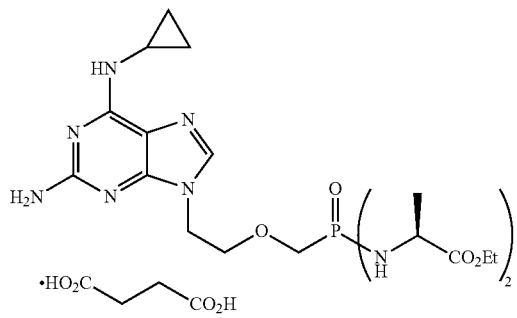

| | |
|---|---|
| Molecular Formula | $C_{21}H_{35}N_8O_6P \cdot C_4H_6O_4$ |
| Molecular Weight | 526.53 |
| Formula Weight | 644.61 |
| Physical Appearance | White powder |
| Melting Point | 130° C. |
| Solubility | >39 mg/ml (pH 4.2-4.7) |

EXAMPLE 2

Table 1 shows anti-proliferation $EC_{50}$ of compound 1 and its metabolites, cpr-PMEDAP (9-(2-phosphonylmethoxyethyl)-$N^6$-cyclopropyl-2,6-diaminopurine), PMEG (9-(2-phosphonylmethoxyethyl) guanine), and PMEDAP (9-(2-phosphonylmethoxyethyl)-2,6-diaminopurine). A variety of compounds that are used for treatment of hematologic malignancies were also tested, including a DNA polymerase inhibitor (ara-C), DNA polymerase/ribonucleotide reductase inhibitors (cladribine, clofarabine, fludarabine, gemcitabine), an adenosine deaminase inhibitor (deoxycoformycin), a DNA methylation inhibitor (decitabine), a DNA alkylator (doxorubicin), and a mitosis inhibitor (vincristine). All compounds, with the exception of doxorubicin and vincristine, are nucleoside analogs; ara-$C_1$ gemcitabine, and decitabine are cytosine analogs and the rest are adenosine analogs. cpr-PMEDAP and PMEG can be considered adenosine and guanosine analogs, respectively. Compounds were tested using human and canine lymphoblasts (stimulated with a T-cell mitogen phytohemagglutinin (PHA) or a B-cell mitogen pokeweed mitogen (PWM)), two T-lymphoid cell lines derived from patients with acute lymphocytic leukemia (CEM and Molt-4), two myeloid cell lines derived from patients with acute myelogenous leukemia (KG-1 and HL-60), two B-lymphoid cell lines derived from Burkitt's lymphoma (Daudi and Raji), a B-lymphoid cell line from non-Hodgkin's lymphoma (RL), a T-lymphoid cell line from cutaneous T-lymphoma (PM-1), and a monocytic cell line from histiocytic lymphoma (U937).

Compound 1 exhibited anti-proliferative activity in a variety of lymphoblasts and leukemia/lymphoma cell lines. Its $EC_{50}$ range was between 27 and 1043 nM, similar to those of clofarabine (25-418 nM) and ara-C (23-1820 nM), two nucleoside analogs commonly used for the treatment of hematologic malignancies. Among other nucleosides, gemcitabine was the most potent (3.4-18 nM) and deoxycoformycin was the least potent (>200,000 nM). Among all compounds, vincristine (0.6-5.3 nM) exhibited the highest potency. There was no significant difference in activity of compound 1 in human and canine cells. In addition, no difference was observed between PHA-blasts (predominantly T-cells) and PWM-blasts (predominantly B-cells) or between T-lymphoid and B-lymphoid cell lines. Thus, unlike another guanosine analogue, nelarabine, which is only effective against T-cell lymphomas, compound 1 may be effective in both T- and B-cell lymphomas.

In most cell types tested, cpr-PMEDAP, which is the hydrolyzed product of compound 1, was significantly less potent than compound 1, suggesting that the phosphoramidate prodrug enhanced entry of the drug into cells, and that the prodrug moiety was cleaved inside cells. PMEG, the deaminated product of cpr-PMEDAP was significantly more potent than the dealkylated product PMEDAP, consistent with the hypothesis that the active molecule for anti-proliferative activity of compound 1 is PMEGpp.

TABLE 1

Anti-Proliferation $EC_{50}$ (nM) In Human Lymphoblasts, Canine Lymphoblasts, And Human Cell Lines Derived From Leukemia/Lymphoma Patients

| | PHA-blast (human T-cells) | PWM-blast (human B-cells) | PHA-blast (canine T-cells) | PWM-blast (canine B-cells) | CEM (T-lymphoid) | Molt 4 (T-lymphoid) | KG-1 (Myeloid) |
|---|---|---|---|---|---|---|---|
| Compound 1 | 135 | 42 | 30 | 14 | 156 | 27.3 | 1043 |
| GS-8369 (cpr-PMEDAP) | 2348 | N.D | N.D | N.D | 2217 | 1473 | 1109 |
| PMEG | 1679 | N.D | N.D | N.D | 5195 | 1739 | 2928 |
| PMEDAP | 8953 | N.D | N.D | N.D | 19874 | 27896 | 7633 |
| Ara-C (Cytarabine) | 1820 | N.D | N.D | N.D | 143 | 23 | 56 |
| Gemcitabine | 9.6 | N.D | N.D | N.D | 21 | 8.5 | 5.7 |
| Clofarabine | 62 | 126 | 146 | 93 | 418 | 25 | 60 |
| Cladribine | 296 | N.D | N.D | N.D | 1167 | 74 | 89 |
| Fludarabine des-phosphate | 1102 | N.D | N.D | N.D | >40,000 | 1550 | 4518 |
| Deoxy coformycin (pentostasin) | >200,000 | N.D | N.D | N.D | N.D | >200,000 | >200,000 |
| Decitabine | 204 | N.D | N.D | N.D | 3004 | 580 | 83 |
| Doxorubicin | 7.6 | N.D | N.D | N.D | N.D | 1.2 | 28 |
| Vincristine | 2.4 | 0.9 | 0.9 | 0.9* | 2 | 0.4 | 3.2 |

| | HL-60 (Myeloid) | RL (B-lymphoid) | Daudi (B-lymphoid) | Raji (B-lymphoid) | PM-1 (T-lymphoid) | U937 (Monocytic) |
|---|---|---|---|---|---|---|
| Compound 1 | 214 | 78 | 27 | 89* | 125 | 394 |
| GS-8369 (cpr-PMEDAP) | 1608 | N.D | 1838 | N.D | 6725 | 4478 |
| PMEG | 3918 | N.D | 994 | 2724 | 4022 | 4009 |
| PMEDAP | 21667 | N.D | 14045 | 24899 | 22732 | 24445 |
| Ara-C (Cytarabine) | 212 | 610 | 209 | 23 | 194 | 38 |
| Gemcitabine | 8.6 | 18 | 6 | 3.4 | 16 | 31 |
| Clofarabine | 73 | 49.5 | 221 | 19.4 | 145 | 37 |
| Cladribine | 50* | 4 | 525 | 12 | 40 | 20 |
| Fludarabine des-phosphate | 1768 | N.D | N.D | N.D | 12857 | 300 |
| Deoxy coformycin (pentostasin) | >200,000 | N.D | N.D | N.D | N.D | >200,000 |
| Decitabine | 3831 | N.D | N.D | N.D | >20,000 | 77 |
| Doxorubicin | 24 | 25 | 3.8 | 8.6 | 29.5 | 13 |
| Vincristine | 2 | 1.4 | 0.6 | 2.5 | 5.3 | 2.8 |

The PHA-lymphoblasts were generated by incubating peripheral blood mononuclear cells (PBMC) with the T-cell mitogen PHA, (1 µg/mL) for 3 days followed by incubation with 10 U/mL interleukin-2 for 4 more days. The PWM-lymphoblasts were generated by incubating B-cells (purified from PBMC using CD19-conjugated magnetic beads) with PWM (20 µg/mL) for 7 days.

Lymphoblasts (150,000 cells per microtiter well) and leukemia/lymphoma cell lines (30,000 cells per well) were incubated with 5-fold serial dilutions of compounds for 3 days. BrdU assay was performed as follows: Lymphoblasts were incubated with 5-fold serial dilutions of compounds in microtiter plates (150,000 cells per well) for 3 days. On Day 3, cells were labeled with 10 µM BrdU for 3 hrs and the amount of BrdU incorporated into cellular DNA was quantified by Enzyme-Linked Immunosorbent Assay (ELISA). Alternatively, cells were incubated with 1 mg/mL XTT reagent (sodium 3,3'-[1[(phenylamino) carbonyl]-3,4-tetrazolium]-bis (4-methoxy-6-nitro) benzene sulfonic acid hydrate) and 1% PMS (phenazine methosulfate) for 2 hrs, and color change (mitochondrial dehydrogenase reduces yellow-colored XTT to orange-colored formazan salt) was quantified. The experimental data were used to generate sigmoidal dose-response curves and 50% effective concentration ($EC_{50}$) values were calculated using GraphPad Prism software version 4.00 for Windows (GraphPad Software, San Diego Calif. USA). Assays were repeated 2-20 times, until the standard error of the mean (SEM) became smaller than 50% of the mean value.

In most cases, assays were repeated 2-20 times until SEM became smaller than 50% of the mean value.

Variable data (SEM>0.5 average $EC_{50}$). N.D; not done.

EXAMPLE 3

Distribution of Prodrugs between PBMCs and Plasma in Dogs

Dogs were administered various prodrugs of cpr-PMEDAP as 0.2 mg/kg 30 minute IV infusions. The prodrugs 1-4 were monoamidates (phosphorus was also substituted with phenoxy), whereas the last two compounds were bis(amidates). The A and B compounds were substantially isolated enantiomers at the phosphorus atom chiral center whereas the monoAlatBU was the racemate at this site. Alanine was the L isomer.

Blood was collected into potassium EDTA and separated by centrifugation. Primary blood mononuclear cells (PBMCs) were collected using CPT tubes (sodium citrate).

For analysis, plasma samples were precipitated by addition of 100 µL acetonitirile containing internal standards (D4AP and TDF) to 100 µL of plasma for prodrug analysis. After protein precipitation by centrifugation, 100 µA was transferred into another tube to be dried and then reconstituted in 100 µL water with 0.2% formic acid. An aliquot of 20 µL was injected onto the column for LC/MS/MS analysis. Analysis was done using a 150× 2.0 mm, 4 µm Synergi Fusion-RP 80A column (Phenomenex) and a multistage linear gradient from 0.5 to 99% acetonitrile in the presence of 0.2% formic acid at 0.25 mL/min. Analytes were detected using a Sciex API-4000 mass spectrometer using electrospray ionization in positive MRM mode. Samples were analyzed for GS-327260, -8369, -0573, and -0438.

PBMC samples were lysed in 70% MeOH. Separate aliquots of cells from each time point resuspended in 100% serum were used to establish the cell quantities in each sample. Cell samples were normalized to $15 \times 10^6$ cells per sample. Varying degrees of hemolyses have been observed. 70% MeOH containing extracted cellular material was split two ways for direct analyses and dephosphorylation and dried separately.

After drying, samples for direct analyses were respuspended in 20% acetonitrile containing internal standards (TDF and D4AP) and analyzed for GS-327260, −8369. 20 µL was injected for LC/MS/MS analysis using a 50×2.0 mm, 4 µm Synergi Hydro-RP 80A column (Phenomenex) and a multistage linear gradient from 0 to 95% acetonitrile in the presence of 0.2% formic acid at 1.0 mL/min. Analytes were detected using a Sciex API-4000 mass spectrometer using electrospray ionization in positive MRM mode.

After drying, samples for dephosphorylation were treated with 1 U of calf intestinal phosphatase (alkaline phosphatase, Sigma) for 2 h in manufacturer provided buffer. Samples were then adjusted to 60% acetonitrile dried and resuspended in 60% acetonitrile containing internal standards (TDF and D4AP) and analyzed for cpr-PMEDAP as described for direct PBMC analysis.

TABLE

Comparison of plasma and PBMC exposure to cpr-PMEDAP (CPMEDAP) following prodrug administration to beagle dog by 30 minute intravenous infusion.

| Compound no. | Prodrug | Plasma CPMEDAP $AUC_{0-24}$ (nM hr) | PBMC CPMEDAP $AUC_{0-24}$ (nM hr) | PBMC to Plasma ratio |
|---|---|---|---|---|
| 1 | MonoAlaiPr | 538 ± 181 | 9,170 ± 450 | 17 |
| 2 | MonoAlatBu | 144 ± 77 | 1,790 ± 468 | 12 |
| 3 | MonoAlatBu(A) | 78 ± 34 | 1,453 ± 1412 | 19 |
| 4 | MonoAlatBu(B) | BLOQ[a] | ND[b] | ND |
| 5 | BisAlaiPr | 4,470 ± 2,040 | 5,380 ± 1,320 | 1.2 |
| CPMEDAP | BisAlaEth | 59 ± 38 | 7,550 ± 3,450 | 130 |

[a]BLOQ = Below the lower limit of quantitation. For CPMEDAP in plasma this value was 20 nM.

[b]ND = Not determined. PBMC samples not collected for compound 4 administration.

We claim:
1. A sterile aqueous solution comprising the succinic acid salt of the compound of formula (I)
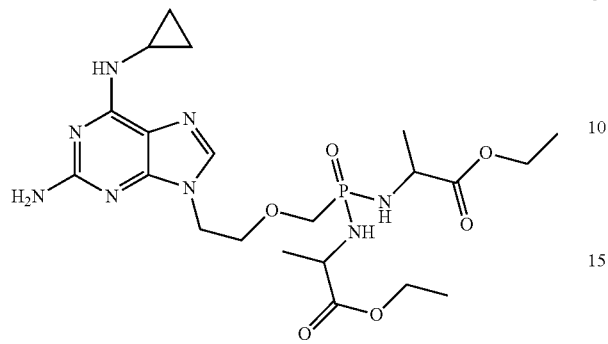
and dextrose.